United States Patent [19]
Dobrin et al.

[11] Patent Number: 5,628,856
[45] Date of Patent: May 13, 1997

[54] METHOD FOR FORMING A COMPOSITE ELASTIC MATERIAL

[75] Inventors: George C. Dobrin; Karen M. Davis, both of Cincinnati, Ohio

[73] Assignee: The Procter & Gamble Company, Cincinnati, Ohio

[21] Appl. No.: 639,821

[22] Filed: Apr. 29, 1996

[51] Int. Cl.$^6$ ............... A61F 13/00; B32B 31/16
[52] U.S. Cl. ............ 156/244.18; 156/161; 156/163; 156/164; 156/229; 156/252; 156/253; 156/244.24; 156/244.26; 428/131; 428/137; 604/385.1; 604/385.2
[58] Field of Search ................. 156/161, 163, 156/164, 229, 252, 253, 285, 244.11, 244.18, 244.19, 244.24, 244.26; 604/385.2, 385.1; 428/131, 137, 138; 264/288.8, 504, 555

[56] References Cited

U.S. PATENT DOCUMENTS

| | | |
|---|---|---|
| 4,062,995 | 12/1977 | Korpman . |
| 4,333,782 | 6/1982 | Pieniak . |
| 4,414,970 | 11/1983 | Berry . |
| 4,456,570 | 6/1984 | Thomas et al. ............... 264/504 X |
| 4,522,863 | 6/1985 | Keck et al. . |
| 4,525,407 | 6/1985 | Ness .............................. 156/229 X |
| 4,535,020 | 8/1985 | Thomas et al. ............... 428/137 X |
| 4,541,794 | 9/1985 | Raley et al. ................... 264/504 X |
| 4,552,709 | 11/1985 | Koger, II et al. ............. 264/504 |
| 4,573,991 | 3/1986 | Pieniak et al. . |
| 4,606,964 | 8/1986 | Wideman . |
| 4,609,518 | 9/1986 | Curro et al. ................... 264/504 |
| 4,720,415 | 1/1988 | Vander Wielen et al. ..... 156/164 X |
| 4,741,877 | 5/1988 | Mullane, Jr. ................... 264/504 |
| 4,878,825 | 11/1989 | Mullane, Jr. ................... 264/504 X |
| 4,977,011 | 12/1990 | Smith . |
| 4,995,930 | 2/1991 | Merz et al. . |
| 5,114,781 | 5/1992 | Morman . |
| 5,209,801 | 5/1993 | Smith . |
| 5,366,782 | 11/1994 | Curro et al. ................... 428/137 |
| 5,368,909 | 11/1994 | Langdon et al. .............. 428/137 |
| 5,368,910 | 11/1994 | Langdon et al. .............. 428/137 |
| 5,441,691 | 8/1995 | Dobrin et al. ................. 264/504 |
| 5,531,729 | 7/1996 | Coles et al. ................... 604/385.2 X |
| 5,591,510 | 1/1997 | Junker et al. ................. 428/137 X |

*Primary Examiner*—Jeff H. Aftergut
*Attorney, Agent, or Firm*—Kevin C. Johnson; Steven W. Miller; Jacobus C. Rasser

[57] ABSTRACT

A method for forming a composite elastic material. An elastic member having at least one elastic strand is fed onto a rotating forming structure exhibiting a multiplicity of apertures therein. The elastic member has a surface facing the forming structure and another surface facing away from the forming structure. A thermoplastic film is extruded onto the surface of the elastic member facing away from the forming structure. A pneumatic vacuum is applied to the thermoplastic film and the elastic member so that the thermoplastic film is simultaneously apertured and bonded to the elastic member thereby forming a breathable composite elastic material.

20 Claims, 4 Drawing Sheets

METHOD FOR FORMING A COMPOSITE ELASTIC MATERIAL

FIELD OF THE INVENTION

The present invention relates to a method for forming a composite elastic material suitable for use in disposable absorbent articles such as disposable diapers, incontinence briefs, training pants, feminine hygiene garments, and the like.

As used herein, the term "composite elastic material" refers to a multilayer or multicomponent material adapted to stretch and recover and which has at least one elastic member, layer or component, such as an elastic scrim, joined to another member, layer or component such as a thermoplastic film.

BACKGROUND OF THE INVENTION

Infants and other incontinent individuals wear disposable absorbent articles such as diapers to receive and contain urine and other body exudates. Absorbent articles function both to contain the discharge materials and to isolate these materials from the body of the wearer and from the wearer's garments and bed clothing. Disposable absorbent articles having many different basic designs are known to the art.

However, absorbent articles have a tendency to sag or gap away from and to slide/slip down on the body of the wearer during wear. This sagging/gapping and sliding/slipping is caused by the relative motions of the wearer as the wearer breathes, moves, and changes positions by the downward forces generated when the absorbent article is loaded with body exudates, and by the deformation of the materials of the absorbent article itself when subjected to such wearer's motions. This sagging/gapping and sliding/slipping of the absorbent article can lead to premature leakage and poor fit of the absorbent article about the wearer in the waist regions and the leg regions of the absorbent article.

In order to more snugly fit absorbent articles about the wearer, certain commercially available absorbent articles have been provided with elasticized waistbands and elasticized side panels. An example of a disposable diaper with elasticized waistbands and elasticized side panels is disclosed in U.S. Pat. No. 5,152,092 issued to Buell et al. on Sep.29, 1992. The elasticized waistband and the elasticized side panels typically comprise an elastic member affixed between portions of the absorbent article, for example, between the topsheet and the backsheet. The elasticized waistband and the elasticized side panels are thus, designed to expand and contract with the wearer's motions to maintain the fit of the absorbent article about the wearer during use.

The incorporation of elastic members into disposable absorbent products such as disposable diapers has increased both the cost of materials and construction of the disposable diapers. In addition, it has been found that absorbent articles having elasticized waistbands and elasticized side panels comprising elastomeric films can make the absorbent article feel hot and uncomfortable to wear because the elastomeric film is impermeable to air and/or moisture thereby making the absorbent article feel hot and uncomfortable in the waist region and in the side panels.

Therefore, it is an object of the present invention to provide a method for forming a composite elastic material which is breathable.

It is another object of the present invention to provide a method for forming a breathable composite elastic material which is suitable for use in a disposable absorbent article.

It is a further object of the present invention to provide a low cost method for forming a composite elastic material.

These and other objectives of the present invention will be more readily apparent when considered in reference to the following description and when taken in conjunction with the accompanying drawings.

SUMMARY OF THE INVENTION

The present invention provides a method for forming a composite elastic material. An elastic member comprising at least one elastic strand is fed onto a rotating forming structure exhibiting a multiplicity of apertures therein. The elastic member has a surface facing the forming structure and another surface facing away from the forming structure. A thermoplastic film is extruded onto the surface of the elastic member facing away from the forming structure and onto the forming structure itself. A pneumatic vacuum is applied to the thermoplastic film and the elastic member so that the thermoplastic film is simultaneously apertured and bonded to the elastic member thereby forming a breathable composite elastic material.

The elastic member preferably comprises a plurality of longitudinal strands and a plurality of transverse strands interconnected to one another. In a preferred embodiment all of the longitudinal and transverse strands are comprised of an elastic material. Alternatively, only the longitudinal strands or only the transverse strands are comprised of an elastic material depending on the desired direction of stretch of the composite elastic material. The other strands which are not elastic are preferably comprised of a thermoplastic material.

BRIEF DESCRIPTION OF THE DRAWINGS

While the specification concludes with claims particularly pointing out and distinctly claiming the subject matter which is regarded as the present invention, it is believed that the invention will be better understood from the following description which is taken in conjunction with the accompanying drawings, in which:

DETAILED DESCRIPTION OF THE INVENTION

As used herein, the term "absorbent article" refers to devices which absorb and contain body exudates, and, more specifically, refers to devices which are placed against the skin of the wearer to absorb and contain the various exudates discharged from the body. The term "disposable" is used herein to describe absorbent articles which are not intended to be laundered or otherwise restored or reused as an absorbent article after a single use, (i.e., they are intended to be discarded and preferably, recycled, composted or otherwise disposed of in an environmentally compatible manner). A "unitary" absorbent article refers to an absorbent article which is formed of separate parts united together to form a coordinated entity so that they do not require separate manipulative parts like a separate holder and liner.

Figure 1:
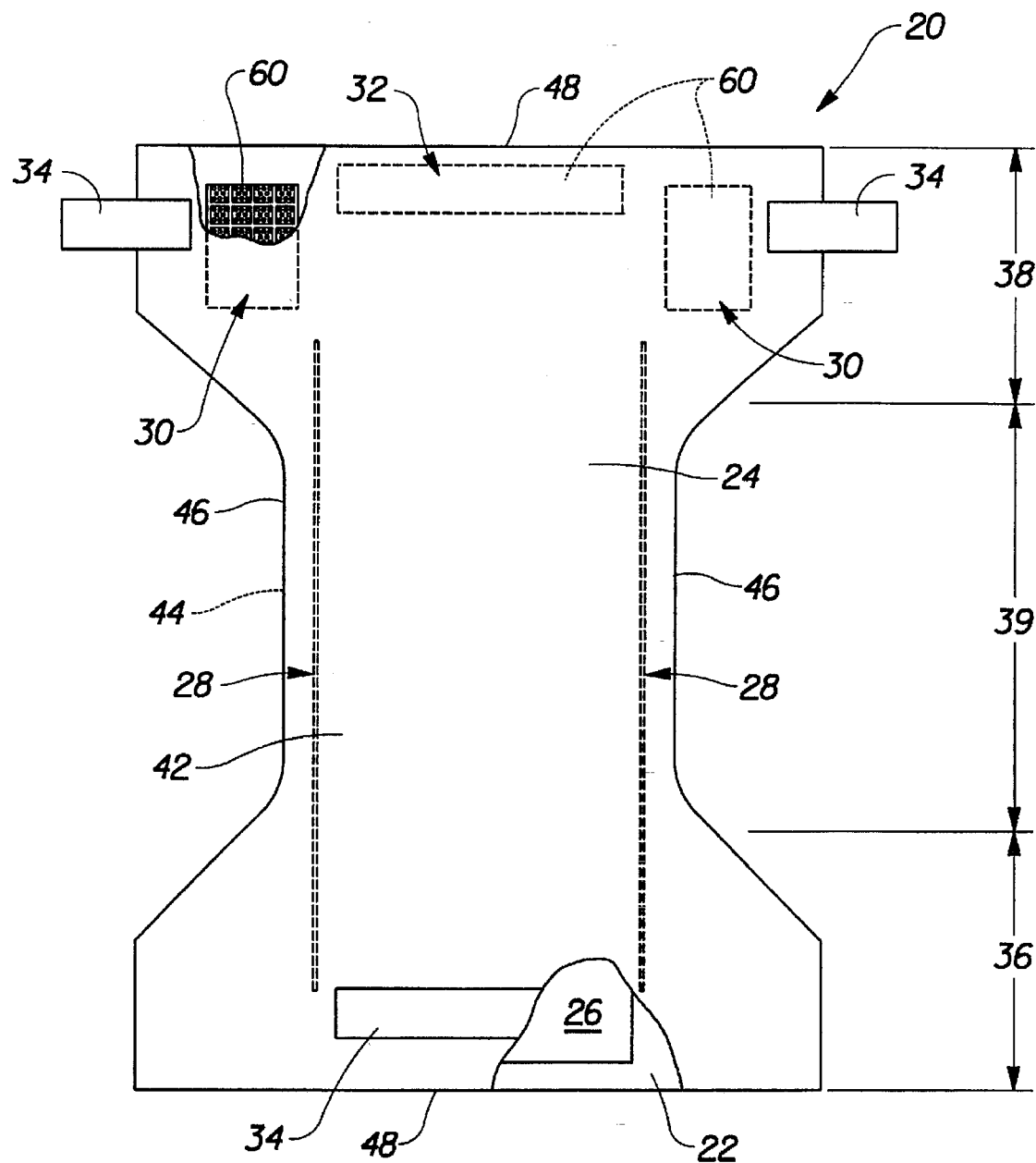
FIG. 1 is a plan view of an absorbent article comprising the composite elastic material formed according to the method of the present invention in the elasticized waistband and in the elasticized side panels.

A preferred embodiment of a unitary absorbent article comprising an elasticized waistband and elasticized side panels each comprising the composite elastic material formed by the method of the present invention is the disposable absorbent article, disposable diaper 20, shown in FIG. 1. As used herein, the term "diaper" refers to an absorbent article generally worn by infants and incontinent persons that is generally worn about the lower torso of the wearer. It should be understood, however, that the present invention is also applicable to other absorbent articles such as incontinence briefs, diaper holders, feminine hygiene garments, training pants, and the like.

With reference to FIG. 1, an absorbent article, such as diaper 20, generally comprises a topsheet 22, a backsheet 24 joined to the topsheet 22, and an absorbent core 26 positioned between the topsheet 22 and the backsheet 24. The diaper 20 preferably further comprises elasticized leg cuffs 28, elasticized side panels 30, an elasticized waistband 32 and a fastening system 34.

The diaper 20 is shown in FIG. 1 to have an outer surface 42 (facing the viewer in FIG. 1), an inner surface 44 opposed to the outer surface 42, a front waist region 36, a rear waist region 38 opposed to the front waist region 36, a crotch region 39 positioned between the front waist region 36 and the rear waist region 38, and a periphery which is defined by the outer perimeter or edges of the diaper in which the longitudinal edges are designated 46 and the end edges are designated 48. The inner surface 44 of the diaper 20 comprises that portion of the diaper 20 which is positioned adjacent to the wearer's body during use (i.e., the inner surface 44 generally is formed by at least a portion of the topsheet 22 and other components joined to the topsheet 22). The outer surface 42 comprises that portion of the diaper 20 which is positioned away from the wearer's body (i.e., the outer surface 42 is generally formed by at least a portion of the backsheet 24 and other components joined to the backsheet 24). As used herein, the term "joined" encompasses configurations whereby an element is directly secured to the other element by affixing the element directly to the other element in configurations whereby the element is indirectly secured to the other element by affixing the element to intermediate member(s) which in turn are affixed to the other element. FIG. 1 shows a preferred embodiment of the diaper 20 in which the topsheet 22 and the backsheet 24 have length and width dimensions generally larger than those of the absorbent core 26. The topsheet 22 and the backsheet 24 extend beyond the edges of the absorbent core 26 to thereby form the periphery of the diaper 20.

The absorbent core 26 may be any absorbent means which is generally compressible, conformable, non-irritating to the wearer's skin, and capable of absorbing and containing liquids such as urine and other body exudates. As shown in FIG. 1, the absorbent core 26 has a garment surface, a body surface, side edges, and waist edges. The absorbent core may be manufactured in a wide variety of sizes and shapes and form a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers including colorer; chemically stiffened, modified, or cross-linked cellulosic fibers; tissue including tissue wraps and tissue laminates; absorbent foams; absorbent sponges; superabsorbent polymers; absorbent gelling material; or any equivalent material or combinations of materials. The configuration and construction of the absorbent core may also be varied (e.g., the absorbent core may have varying caliper zones, a hydrophilic gradient, a superabsorbent gradient, or a lower average density and lower average basis weight acquisition zones; or may comprise one or more layers or substrates). The total absorbent capacity of the absorbent core, should, however, be compatible with the design loading and the intended use of the diaper 20. Further, the size and absorbent capacity of the absorbent core may be varied to accommodate wearers ranging from infants through adults.

The backsheet 24 is preferably impervious to liquids (e.g., urine) and is preferably manufactured from a flexible material. As used herein, the term "flexible" refers to materials which are compliant and will readily conform to the general shape and contours of the human body. The backsheet prevents the exudates absorbed and contained in the absorbent core from wetting articles which contact the diaper 20 such as bed sheets and undergarments. The backsheet may thus comprise a woven or nonwoven material, polymeric films such as thermoplastic films of polyethylene or polypropylene, or composite material such as a film-coated nonwoven material. Preferably, the backsheet is a thermoplastic film having a thickness of from about 0.012 mm (0.5 mil) to about 0.051 mm (2.0 mils). The backsheet is preferably embossed and/or matte finished to provide a more clothlike appearance. Further, the backsheet may permit vapors to escape from the absorbent core (i.e., breathable) while still preventing exudates from passing through the backsheet.

The topsheet 22 is compliant, soft feeling and non-irritating to the wearer's skin. Further, the topsheet is liquid pervious permitting liquids (e.g., urine) to readily penetrate through its thickness. A suitable topsheet may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Preferably, the topsheet is made of a hydrophobic material to isolate the wearer's skin from the liquids contained in the absorbent core. There are a number of manufacturing techniques which may be used to manufacture the topsheet. For example, the topsheet may be a nonwoven web of fibers, spunbonded, carded, wet-laid, meltblown, hydroentangled, combinations of the above or the like. A preferred topsheet comprises a carded nonwoven web of synthetic fibers.

The elasticized waistband 32 preferably comprises a portion of the topsheet 22, a portion of the backsheet 24 and a composite elastic material 60 positioned between the topsheet 22 and the backsheet 24. The elasticized side panel 30 preferably comprises a portion of the topsheet 22, a portion of the backsheet 24 and a composite elastic material 60 positioned between the topsheet 22 and the backsheet 24.

The composite elastic material 60 is preferably joined to the topsheet 22 and the backsheet 24 by attachment means such as those well known in the art. For example, the composite elastic material 60 may be secured to the topsheet 22 and/or the backsheet 24 by a continuous layer of adhesive, a patterned layer of adhesive, or an array of separate lines, spirals or spots of adhesive. The attachment means will preferably comprise an open pattern network of filaments of adhesive as is disclosed in U.S. Pat. No. 4,573,986 issued to Minetola and Tucker on Mar. 4, 1986, and which is incorporated herein by reference. An exemplary attachment means of an open pattern network of filaments comprises several lines of adhesive filaments swirled into a spiral pattern such as illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

Figure 2:
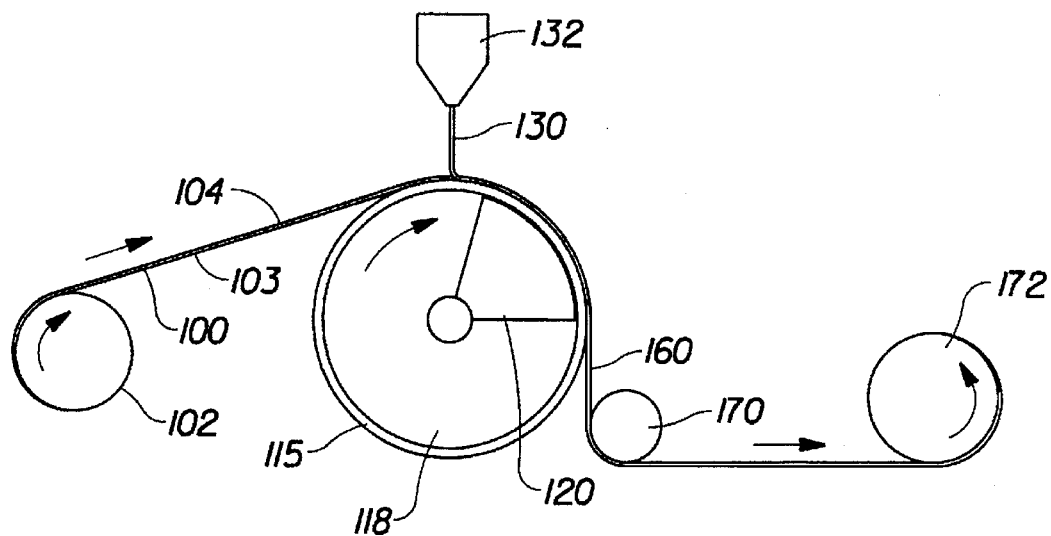
FIG. 2 is a simplified side elevation view showing a method for forming the composite elastic material of the present invention.

A particularly preferred process for forming the composite elastic material of the present invention is illustrated in FIG. 2. In the embodiment shown in FIG. 2, an elastic member 100 comprising at least one elastic strand, preferably a plurality of elastic strands is fed from a supply roll 102 onto the surface of a forming drum 118 about which a forming structure 115 continuously rotates at substantially the same speed as the incoming elastic member. The forming drum 118 preferably includes an internally located vacuum chamber 120 which is preferably stationary relative to the moving forming structure 115.

Figure 3:
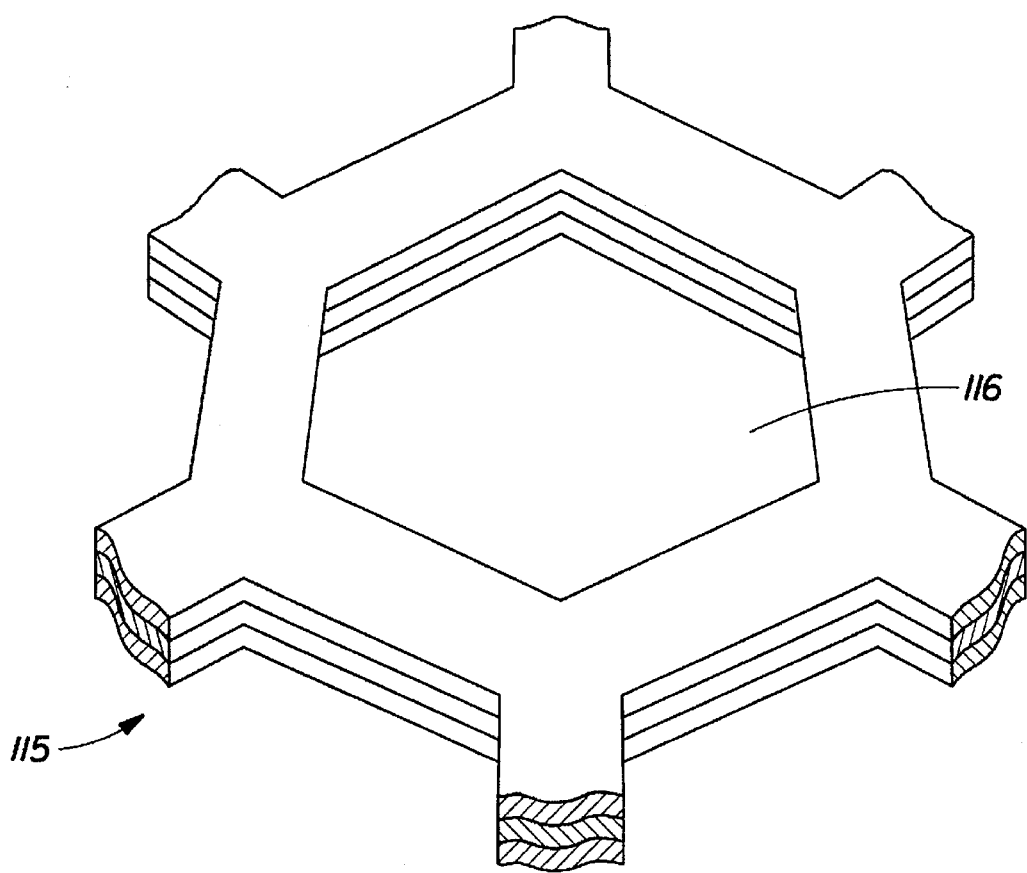
FIG. 3 is an enlarged fragmentary perspective illustration of a forming structure of the present invention.

Referring now to FIG. 3 there is shown a greatly enlarged fragmentary segment of forming structure 115. Forming structure 115 includes a plurality of apertures 116. The forming structure 115 exhibits a fiber-like cross-section of a type generally disclosed in commonly assigned U.S. Pat. No. 4,342,314 issued to Radel et al. on Aug. 3, 1982, which patent is hereby incorporated herein by reference. The forming structure 115 may have various aperture sizes, aperture shapes, and aperture densities. The aperture spacing may be in a regular pattern or it may vary randomly, as desired. Examples of other suitable forming structures are disclosed in commonly assigned U.S. Pat. No. 4,609,518 issued to Curro et al. on Sep. 2, 1986, which patent is hereby incorporated herein by reference.

Referring again to FIG. 2 as the elastic member 100 is fed onto the forming drum 118 about which forming structure 115 continuously rotates, one surface 103 of elastic member 100 faces the forming structure 115 and directly contacts the forming structure 115 while the other surface 104 of elastic member 100 faces away from the forming structure 115. As the forming structure 115 rotates, a thermoplastic film 130 is extruded from extruder 132 directly onto the surface 104 of the elastic member 100 facing away from forming structure 115. The vacuum chamber 120 subjects the elastic member 100 and the thermoplastic 130 film to a pneumatic vacuum. The pneumatic vacuum sucks portions of the thermoplastic film into the apertures 116 of the forming structure 115 thereby forming apertures in the thermoplastic film. In addition, the vacuum pulls the thermoplastic film against the elastic member thereby bonding the thermoplastic film to the elastic member to form a breathable composite elastic material 160. The composite elastic material 160 is then removed from the surface of the forming structure 115 about an idler roll 170 and is taken up on wind up roll 172.

Figure 4:
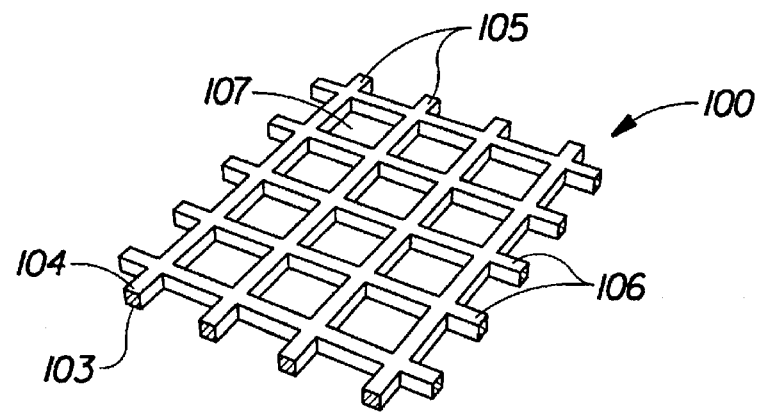
FIG. 4 is an enlarged fragmentary perspective illustration of a preferred elastic member of the present invention.

Referring now to FIG. 4 there is shown an enlarged fragmented perspective illustration of a preferred elastic member, elastic scrim 100. As seen in FIG. 4, the elastic scrim 100 comprises a plurality of elastic strands 105 extending in a first or longitudinal direction and a plurality of elastic strands 106 extending in a second or transverse direction perpendicular to the first direction. The longitudinal strands 105 and the transverse strands 106 are interconnected to one another. The elastic scrim 100 has a plurality of openings or apertures 107 distributed therein to produce a net-like construction. The elastic strands 105 and 106 are shown in FIG. 4 to be oriented to produce openings 107 having a generally square configuration. However, elastic strands 105 and 106 may be arranged to produce openings of other configurations such as rectangular, diamond, etc. The elastic scrim 100 of the present invention need not have the symmetrical, regular array of apertures of a reticulated member, but may merely include a plurality of interconnected elastic elements defining apertures therebetween. Depending on the properties of the elastic material including the modulus of elasticity and the thickness and width of the elastic strands 105 and 106, the number of openings 107 may vary from 2 to 100 openings per linear inch in both the longitudinal and transverse direction of the elastic member 100. In addition, the elastic strands 105 and 106 may be of different widths in the longitudinal or transverse direction, and the spacing between the elements may vary from the transverse to the longitudinal direction. The thickness of the elastic scrim 100 is preferably from about 1 mil to about 50 mils and more preferably from about 5 mils to about 20 mils.

Examples of suitable elastic scrims are disclosed in U.S. Pat. No. 4,062,995 issued to Korpman on Dec. 13, 1977; and in U.S. Pat. No. 4,573,991 issued to Pieniak et al. on Mar. 4, 1986.

Examples of suitable materials for use as the elastic strands 105 and 106 include but are not limited to elastomeric foams, "live" synthetic or natural rubber, and lycra. In some embodiments it may be necessary for both elastic strands 105 and 106 to be elastic. This is true where it is desirable to provide stretch in multiple directions. However, in other embodiments, it may be necessary for only one of the strands, either one of strands 105 or 106 to be elastic. This is true where it is desirable to provide stretch in only one direction. In those situations where it is desirable to provide stretch in only one direction, at least one of the elastic strands, for example elastic strand 105, need be elastic. The other elastic strand, for example elastic strand 106, may be made from a wide variety of other materials. Examples of suitable materials for use as the non-elastic strands 106 include but are not limited to thermoplastic materials such as polyethylene, polypropylene, and polyester and the like.

Figure 5:
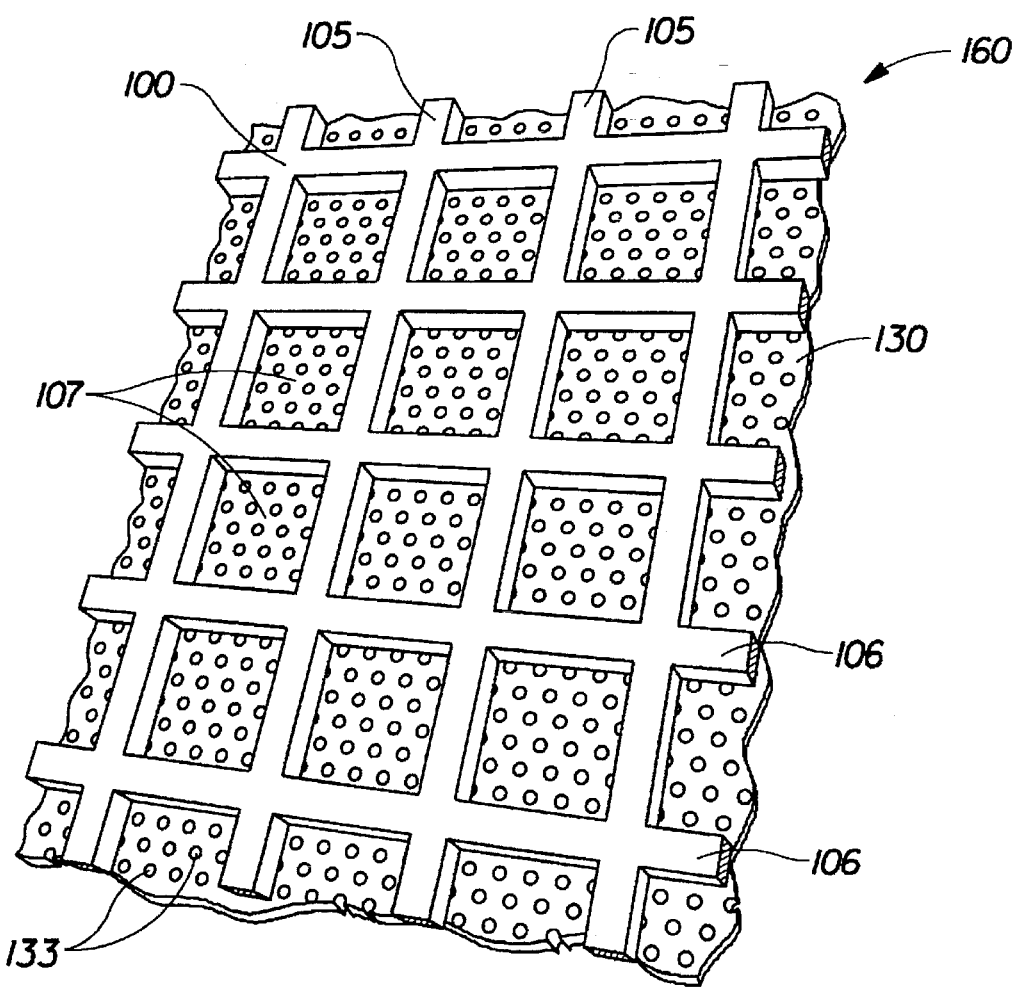
FIG. 5 is an enlarged fragmentary perspective illustration of a composite elastic material formed according to the method of the present invention.

Referring now to FIG. 5, there is shown a fragmented perspective illustration of the breathable composite elastic material 160. As seen in FIG. 5 the breathable composite elastic material 160 comprises the elastic member 100 comprising interconnected elastic strands 105 and 106 bonded to apertured thermoplastic film 130. Apertured film 130 comprises a plurality of apertures 133 generally corresponding to apertures 116 in forming structure 115, as shown in FIG. 3.

The apertures 133 in the apertured film 130 are preferably smaller in size than the openings 107 of the elastic member 100. However, the apertures 133 may be the same size as the openings 107 or larger than the openings 107 in the elastic member 100.

The apertures 133 in the composite elastic material 160 allow the composite to be breathable permitting the passage and air and vapor. When used as the elastic component of the elasticized waistband and/or the elasticized side panels, the composite elastic material is both as elastic, breathable, and relatively low cost compared to traditional elastic materials.

Figure 6:
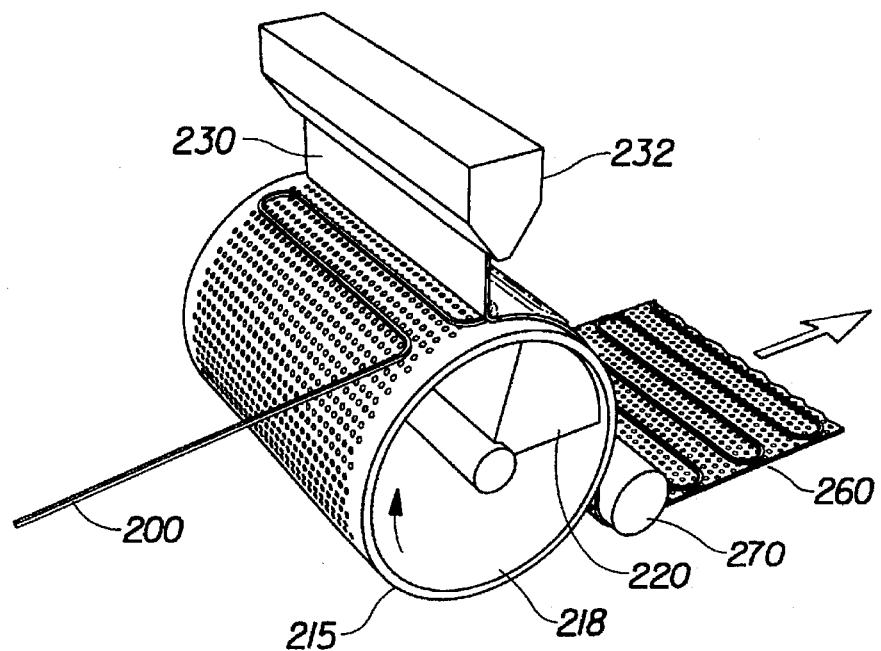
FIG. 6 is a simplified perspective view showing another method for forming a composite elastic material of the present invention.

An alternative process for forming a composite elastic material of the present invention is illustrated in FIG. 6. In the embodiment shown in FIG. 6, a single elastic strand 200 is fed from a supply source, (not shown for simplicity), onto the surface of a forming drum 218 about which a forming structure 215 continuously rotates. The forming drum 218 includes an internally located vacuum chamber 220 which is preferably stationary relative to the moving forming structure 215. A suitable forming structure is forming structure 115 shown in FIG. 3.

As the elastic strand 200 is fed onto the forming drum 218 about which the forming structure 215 continuously rotates, the elastic strand 200 is preferably oscillated in a back and forth motion to extend the elastic strand 200 from one edge of the forming structure 215 to the opposite edge of the forming structure 215. While not shown for simplicity, any suitable means for oscillating the elastic strand 200 may be used. As the forming structure 215 rotates, a thermoplastic film 230 is extruded from extruder 232 directly onto the surface of the elastic strand 200 facing away from the forming structure 215. The vacuum chamber 220 subjects the elastic strand and the thermoplastic film to a pneumatic vacuum. The pneumatic vacuum sucks portions of the thermoplastic film into the apertures of the forming structure 215 thereby forming apertures in the thermoplastic film. In addition, the vacuum pulls the thermoplastic film against the elastic strand 200 thereby bonding the thermoplastic film to the elastic strand to form a breathable composite elastic material 260. The breathable composite elastic material 260 is then removed from the surface of the forming structure 215 about an idler roll 270 and is preferably taken up on a wind up roll, (not shown for simplicity).

In the embodiment of FIG. 6 a single elastic strand is shown. Alternatively, multiple elastic strands may be fed in an oscillating manner onto the forming structure 215. For example, two, three, four or more elastic strands may be fed in an oscillating manner onto the forming structure 215.

Figure 7:
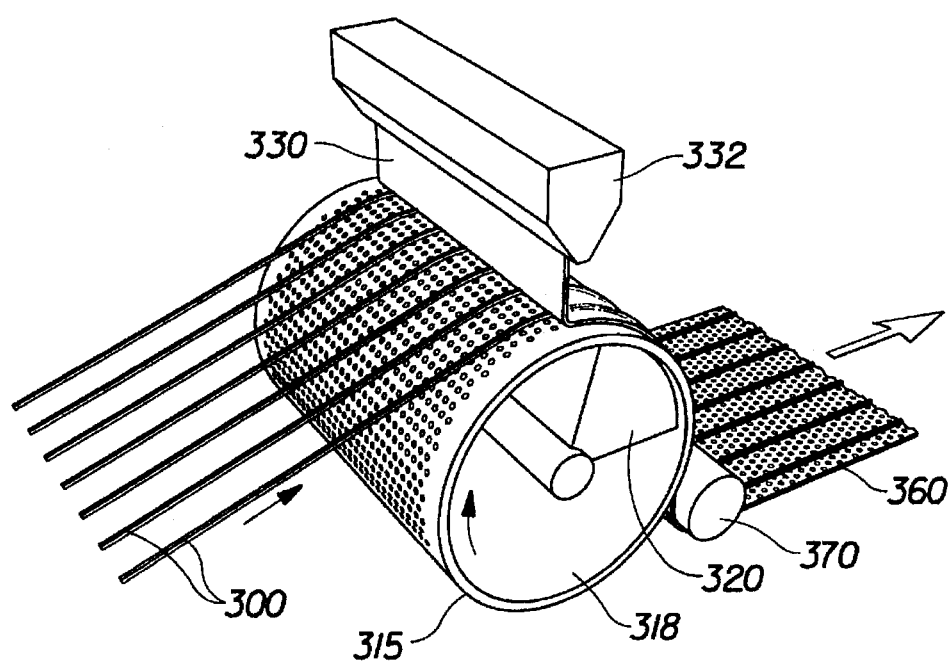
FIG. 7 is a simplified perspective view showing another method for forming a composite elastic material of the present invention.

Another process for forming a composite elastic material of the present invention is illustrated in FIG. 7. In the embodiment shown in FIG. 7, an elastic member 300 comprising a plurality of elastic strands is fed from a supply source, (not shown for simplicity), onto the surface of a forming drum 318 about which a forming structure 315 continuously rotates. The forming drum 318 includes an internally located vacuum chamber 320 which is stationary relative to the moving forming structure 315. A suitable forming structure 315 is forming structure 115 shown in FIG. 3.

The elastic member 300 comprises a plurality of individual elastic strands preferably spaced apart from one another. In the embodiment shown in FIG. 7, the elastic member 300 comprises seven individual elastic strands. However, any suitable number of individual elastic strands may be used. Unlike the method shown in FIG. 6, the individual elastic strands of the elastic member 300 in FIG. 7 are not oscillated in a back and forth motion. Instead, the individual elastic strands of elastic member 300 are simply fed onto the forming structure 315 from a supply source.

As the forming structure 315 rotates, a thermoplastic film 330 is extruded from extruder 332 directly onto the surface of the elastic member 300 facing away from the forming structure 315. The vacuum chamber 320 subjects the elastic as member and a thermoplastic film to a pneumatic vacuum. The pneumatic vacuum sucks portions of the thermoplastic film into the apertures of the forming structure thereby forming apertures in the thermoplastic film. In addition, the vacuum pulls the thermoplastic film against the elastic member thereby bonding the thermoplastic film to the elastic member to form a breathable composite elastic material 360. The breathable composite elastic material 360 is removed from the surface of the forming structure 315 about an idler roll 370 and taken up on a wind up roll (not shown for simplicity).

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for forming a composite elastic material, said method comprising the steps of:
   a) feeding an elastic member comprising at least one elastic strand onto a rotating forming structure exhibiting a multiplicity of apertures therein, said elastic member having a surface facing said forming structure and a surface facing away from said forming structure;
   b) extruding a thermoplastic film onto the surface of the elastic member facing away from the forming structure; and
   c) applying a pneumatic vacuum to the thermoplastic film and the elastic member so that the thermoplastic film is simultaneously apertured and bonded to the elastic member while still on said forming structure.

2. The method of claim 1 wherein said elastic member comprises an elastic scrim.

3. The method of claim 1 wherein said elastic member comprises a plurality of longitudinal strands and a plurality of transverse strands interconnected to one another.

4. The method of claim 3 wherein said longitudinal strands comprise an elastic material.

5. The method of claim 4 wherein said transverse strands comprise a thermoplastic material.

6. The method of claim 3 wherein said transverse strands comprise an elastic material.

7. The method of claim 6 wherein said longitudinal strands comprise a thermoplastic material.

8. The method of claim 1 wherein said composite elastic material forms a portion of an absorbent article.

9. The method of claim 8 wherein said composite elastic material forms an elasticized waistband in said absorbent article.

10. The method of claim 8 wherein said composite elastic material forms an elasticized side panel in said absorbent article.

11. A method for forming a composite elastic material, said method comprising the steps of:
   a) feeding an elastic member comprising at least one elastic strand onto a rotating forming structure exhibiting a multiplicity of apertures therein, said elastic member having a surface facing said forming structure and a surface facing away from said forming structure;
   b) extruding a thermoplastic film onto the surface of the elastic member facing away from the forming structure; and
   c) simultaneously aperturing the thermoplastic film and bonding the thermoplastic film to the elastic member while still on said forming structure.

12. The method of claim 11 wherein said elastic member comprises an elastic scrim.

13. The method of claim 11 wherein said elastic member comprises a plurality of longitudinal strands and a plurality of transverse strands interconnected to one another.

14. The method of claim 13 wherein said longitudinal strands comprise an elastic material.

15. The method of claim 14 wherein said transverse strands comprise a thermoplastic material.

16. The method of claim 13 wherein said transverse strands comprise an elastic material.

17. The method of claim 16 wherein said longitudinal strands comprise a thermoplastic material.

18. The method of claim 11 wherein said composite elastic material forms a portion of an absorbent article.

19. The method of claim 18 wherein said composite elastic material forms an elasticized waistband in said absorbent article.

20. The method of claim 18 wherein said composite elastic material forms an elasticized side panel in said absorbent article.

* * * * *